United States Patent [19]

Yoshida et al.

[11] Patent Number: 4,964,734
[45] Date of Patent: Oct. 23, 1990

[54] MOISTURE CONTENT MEASURING SYSTEM

[75] Inventors: Hiroshi Yoshida, Ichinomiya; Takeki Noguchi, Aichi; Masahiko Ichikawa, Okazaki; Takemi Nakane; Kyoji Kubo, both of Hiroshima; Kenichiro Kinoshita, Tokyo, all of Japan

[73] Assignees: Chubu Electric Power Company Inc., Aichi; Mitsubishi Jukogyo Kabushiki Kaisha, Tokyo, both of Japan

[21] Appl. No.: 347,903

[22] Filed: May 5, 1989

[30] Foreign Application Priority Data

May 10, 1988 [JP] Japan .................. 63-111535

[51] Int. Cl.⁵ ............................................. G01N 25/56
[52] U.S. Cl. .................................. 374/14; 73/73; 177/245
[58] Field of Search ................... 374/14; 177/245; 219/10.55 B; 73/73

[56] References Cited

U.S. PATENT DOCUMENTS

| | | | |
|---|---|---|---|
| 3,292,417 | 12/1966 | Hayden et al. | 374/14 |
| 4,165,633 | 8/1979 | Raisanen | 177/245 X |
| 4,616,425 | 10/1986 | Burns | 324/65 R X |
| 4,681,996 | 7/1987 | Collins et al. | 374/14 X |
| 4,889,201 | 12/1989 | Oldendorf et al. | 73/73 |

*Primary Examiner*—Daniel M. Yasich
*Attorney, Agent, or Firm*—Wenderoth, Lind & Ponack

[57] ABSTRACT

In order to make it possible to measure the moisture content of coal on an on-line basis with a high degree of precision, a moisture content measuring system including a sample container for holding a sample, a weighing instrument having a turntable adapted to rotate with the sample container placed thereon, an A/D converter responsive to a signal from the weighing instrument, a calculator responsive to a signal from the A/D converter for calculating the moisture content of the sample, an indicator responsive to a signal from the calculator and a microwave generating and irradiating apparatus for heating the sample, is improved. The improvements reside in that the system includes a hot gas generator for heating the sample with hot gas at a low temperature, and a dehumidified dry air circulating means for removing moisture from the sample.

6 Claims, 2 Drawing Sheets

MOISTURE CONTENT MEASURING SYSTEM

BACKGROUND OF THE INVENTION

1. Field of the Invention:

The present invention relates to a moisture content measuring system for analyzing, on an on-line basis, moisture content of coal in a coal burning boiler, of coke in a coal or iron manufacturing plant or of lime, coal or the like in a cement manufacturing plant.

2. Description of the Prior Art:

In most of the coal burning thermal power stations, many kinds of coal are used as mixed together. In order to efficiently burn coal and to smoothly perform a desmoking treatment operation, delicate operation control adapted to the nature of the coal is necessary. Normally, coal is stored as classified depending upon its brand, and the thermal power station is operated by determining a coal mixing proportion on the basis of results of analysis of the respective brands. However, since coal is solid, a broad distribution of quality exists even among the same brand of coal, and for an appropriate use of mixed coal and for combustion control, on-line analysis, from which results can be obtained with a high degree of precision and moreover quickly, is desired. Among other things, with regard to moisture in coal, a moisture content value would vary largely even in the same lot, as influenced by liquid sprinkled for preventing the scattering of coal dust during coal storage and by rainfall, and so, it is considered to be especially important to achieve on-line analysis.

A moisture content measuring process for coal is prescribed in JIS M8811 (Japanese Industrial Standard), 1976, and according to this process, a predetermined amount of sample coal representing a lot of coal is picked up. After the sample has been preliminarily dried at a temperature of 35° C. or lower, it is pulverized and subjected to sample reduction. Then, a pulverized sample having a grain size of 3 mm or less or a grain size of 9.5 mm or less is held within a dryer until it assumes a constant weight at 107° C., and a total moisture content is calculated from the total amount of reduced weight due to drying.

Regarding moisture content measuring apparatuses, other than an apparatus relying upon the above-mentioned JIS process, an infrared moisture meter making us of infrared rays, an electrostatic capacity type moisture meter making use of the correlation between a moisture proportion and a dielectric constant, a microwave moisture meter making use of the absorption of microwaves by moisture, a neutron moisture meter making use of the moderation and scattering of neutrons by hydrogen atoms, and the like are known. And other than with coal, such apparatuses are widely used as apparatuses for performing on-line analysis, such as in the measurement of a degree of dryness of cereals, papers, woods, etc.

In addition, a microwave heat-drying moisture meter, in which an article is dried by irradiating microwaves and a moisture content is calculated from a reduced weight, is sold in the market.

In the moisture measurement according to the above-mentioned JIS process in the prior art, apart from the precision of analysis, normally a half day is necessary for measuring a total moisture content, and so, it takes far longer than 0.5-1 hours which is considered to be desirable for operation and control of a boiler. On the other hand, although the on-line analyzing processes in the prior art had an advantage that results of measurement could be obtained almost on a real-time basis, every one of the processes had a large measurement error and were not respectively practical in that the infrared moisture meter could measure only a moisture content in a surface portion, in that in the electrostatic capacity type moisture meter and the microwave moisture meter the influence of a bulk density upon the measured value was large, and in that in the neutron moisture meter there existed absorption by hydrogen atoms in coal besides the absorption by the moisture. In addition, while the microwave heat-drying moisture meter sold in the market was composed of a microwave source and a ventilation fan in combination, a water dammy circulating section in which water is circulated in a loop through the casing to absorb and exhaust excess energy from the microwave source, an automatic weighing section, a turntable, and a controller-calculator section for the system and it could dry a sample in 1-3 minutes and automatically perform a calculation to obtain a moisture content value, it involved the following problems.

(1) Since the object of measurement is an article having a relatively uniform distribution of moisture including foods such as milk, butter, cheese or the like and powdered or granular medicines, the moisture meter can be applied only to a sample amount of as little as 1-10 g; it cannot measure a large amount of sample (for instance, a sample of 1 kg or more) to which the present invention is directed.

(2) Heating a sample depends solely upon heating by microwave absorption. In the case of a sample of coal having a range of grain sizes as broad as several tens of micrometers to several tens of millimeters, and moreover, having different shapes and sizes, uniform heating is difficult and the sample is locally overheated midway during the moisture measurement. Hence, decomposition of coal and the like occurs, and therefore, an accurate moisture content value cannot be obtained.

(3) Accordingly, the above-mentioned moisture meter employs a system in which a drying period is controlled by a preset timer, and so, it is necessary that a drying time should be preliminarily known for the respective samples.

SUMMARY OF THE INVENTION

It is therefore one object of the present invention to provide a moisture content measuring system, in which a sample can be heated so as not to be decomposed and moisture generated by heating the sample can be quickly removed and measured.

Another object of the present invention is to provide a moisture content measuring system, in which the moisture content of coal or the like being conveyed to a boiler, etc. can be easily sampled and can be measured in a short period of time, so as to achieve on-line processing.

According to a principal feature of the present invention, there is provided a moisture content measuring system, in which as heat for heating a sample such as coal, microwave irradiation and a stream of hot gases are employed in combination. Thus, by reducing a load of microwaves the sample is dried at a temperature lower than a decomposition temperature of coal, and therefore, a moisture content measurement can be taken quickly and with a high degree of precision.

According to a more specific feature of the present invention, there is provided a moisture content measuring system including a sample container for holding a sample, a weighing instrument. having a turntable adapted to rotate with the sample container placed thereon, an A/D converted responsive to a signal from the weighing instrument, a calculator responsive to a signal from the A/D converter for calculating a moisture content in the sample, an indicator responsive to a signal from the calculator, and a microwave generator and irradiating apparatus for heating the sample, which system comprises hot gas generator means for heating the sample at a lower temperature, and dehumidifying means for removing moisture evaporated from the sample.

According to the present invention, owing to the above-featured provisions, a sample such as coal or the like is heated up to a predetermined temperature by microwaves and hot streams of gas generated by the hot gas generator means, and moisture generated from the sample is removed by the dehumidifying means. On the other hand, the sample is always weighed by the weighing instrument. Thus, the moisture content of the sample is calculated by the calculator, and the results of such measurement are sent to the indicator.

Through the above-mentioned process, the sample can be heated so as not to be decomposed, and moisture generated thereby can be removed quickly and can be measured.

In this way, moisture contained in coal or the like being conveyed to a boiler or the like is sampled and measured within a short period of time, and therefore, on-line processing becomes possible.

The above-mentioned and other objects, features and advantages of the present invention will become more apparent by referring to the following description of one preferred embodiment of the invention in conjunction with the accompanying drawings.

DETAILED DESCRIPTION OF THE PREFERRED EMBODIMENT

Now one preferred embodiment of the present invention will be described with reference to FIGS. 1 to 3.

Figure 1:
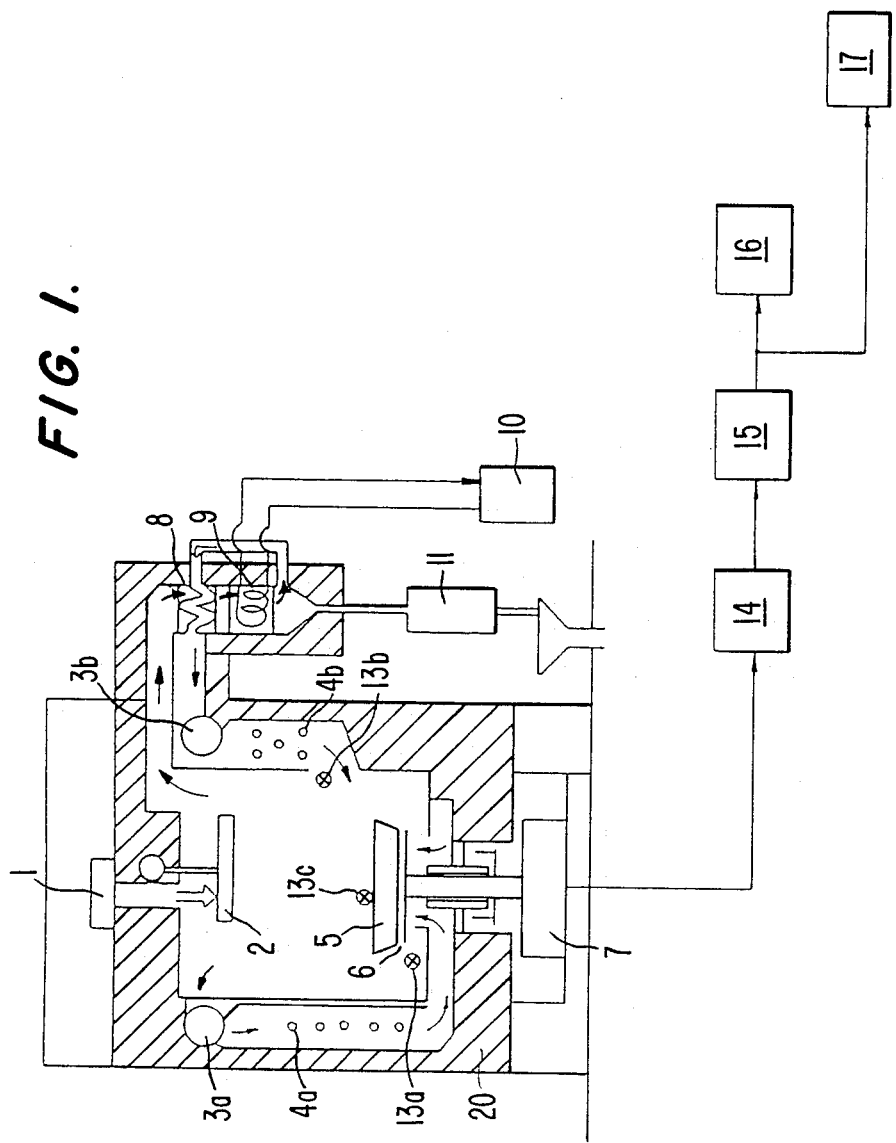
FIG. 1 is a schematic view of one preferred embodiment of the present invention.
Figure 2:
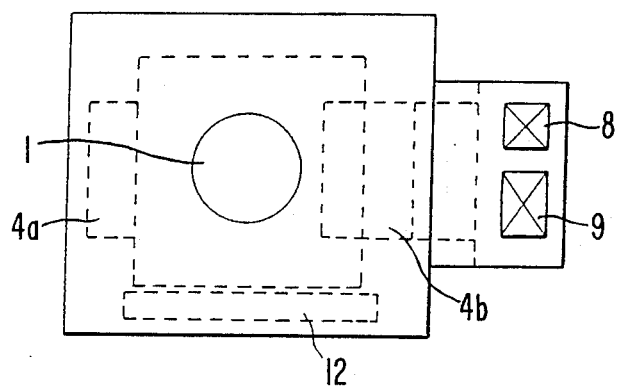
FIG. 2 is a plan view of the same.

Referring to FIGS. 1 and 2, within a casing 20 covered by heat-insulating material is disposed a turntable 6 having a horizontal rotary surface, and this turntable 6 is coupled to a weighing instrument 7 provided thereunder by the intermediary of a shaft projecting through the bottom wall of the casing 20. The output of the weighing instrument 7 is issued to a digital indicator 16 and a display-recorder 17 in a boiler operating room successively through an A/D converter 14 and a calculator 15. The above-mentioned casing 20 has a shutter 12 in its one side wall (FIG. 2), while within two other opposed side walls are disposed a plurality of heaters 4a and 4b, respectively, and fans 3a and 3b at the upper corners. The hot gas is guided through respective ducts, and one stream of gas may be blown out upwards from beneath the turntable 6, while another stream of gas may be blown out from a duct, having an outlet above turntable 6, in a direction onto the turntable 6. Furthermore, thermometers 13a, 13b and 13c are disposed at the periphery of the turntable 6, at the outlet of the duct to the side of a first heat-exchanger 8, and in a sample, and they are respectively connected to a sequence controller (not shown).

Furthermore, a first heat-exchanger 8 and a second heat-exchanger 9 covered by a wall made of heat-insulating material are provided outside of one side wall on the side of the fan 3b. The first heat-exchanger 8 is positioned above the second heat-exchanger 9. And thus, there is provided a structure for performing the so-called gas-gas heat exchange, in which hot gas around the sample may pass through a cell side space (or a tube) of the first heat-exchanger 8 and cold gas having passed through the second heat-exchanger 9 may pass through a tube (or a cell side space) of the first heat-exchanger 8. Whereas the second heat-exchanger 9 is disposed under the first heat-exchanger 8, and it is arranged such that a stream of hot gas precooled by the first heat-exchanger 8 may pass through a cell side space while a circulating coolant cooled by a chiller 10 at the outside may pass through a tube, the second heat-exchanger 9 is adapted to further cool and dehumidify the stream of hot gas pre-cooled by the first heat-exchanger 8. In addition, a cold gas outlet of the second heat-exchanger 9 and the tube (or the cell side space) of the first heat-exchanger 8 are connected via a duct, and they communicate with the duct of the fan 3b.

The bottom of the second heat-exchanger 9 has a funnel shape, and a hole at the bottom end extends through the casing 20 to be open to a drain trap 11 disposed outside of the casing 20.

Furthermore, at the top of the casing 20 is disposed a magnetron 1, whose radiation port extends through the casing 20 and is directed towards the upper surface of the turntable 6. In addition, in the vicinity of the same radiation port is provided a stirrer 2. It is to be noted that in the case where a coal sample weighs about 5 kg at maximum, the weighing instrument 7 is assumed to have a precision of about 1 g. In order to maintain the temperature within the casing 20 at 140°-150° C., the powers of the heaters 4a and 4b and the magnetron 1 are chosen to be 1-3 kW, respectively.

In the operation of the system having the above-described structure, a sample of, for instance, about 1 kg of coal is picked up in the sample container 5, then shutter 12 is opened to place the sample container 5 on the turntable 6, and the shutter 12 is closed. Weighing is commenced by means of the weighing instrument 7, and subsequently the turntable 6 is rotated at a speed of 5-6 r.p.m. The heaters 4a and 4b, the fans 3a and 3b, the first heat-exchanger 8, the second heat-exchanger 9 and the chiller 10 are put in a working condition. Then, power is supplied to the magnetron 1, and irradiation of microwaves is commenced while rotating the stirrer 2 for uniformly irradiating the sample with microwaves. On the other hand, temperatures are measured by the thermometers 13a, 13b and 13c, and an adjustment is effected to maintain the temperature within the casing 20 at 140°-150° C. Furthermore, an output of the magnetron 1 is regulated so that the temperature of the sample may not rise up to about 200° C. or higher. The operations during this period are all controlled by a sequence controller (not shown). A signal representing a variation of the weight of the sample caused by drying is sent via the A/D converter 14 to the calculator 15, whereby a moisture content value changing moment by moment is indicated by the digital indicator 16. Also, the results of measurement are transmitted to the display-recorder 17 in a boiler operating room.

As described above, the sample of coal is heated by microwaves from magnetron 1 so as not to exceed the decomposition temperature of 200° C., and by hot gases generated by the heaters 4a and 4b and the fans 3a and 3b (hot gas generator), in combination, which elements constitute the heating means of the present invention. On the other hand, the hot gas at the periphery of the sample is led to the first heat-exchanger 8, then it passes through a cell side space (or a tube) of the first heat-exchanger 8 and the second heat-exchanger 9, and passes through the tube (or the cell side space) of the first heat-exchanger 8 (whereupon the hot gases are dehumidified and moisture is collected in trap 11), the fan 3b and the heater 4b, and is returned to the periphery of the sample. The first heat-exchanger 8 and the second heat-exchanger 9 thus constitute the dehumidifying means of the present invention. In this way, since the hot gas at the periphery of the sample is continuously circulated and dehumidified, the drying of the sample can be quickened.

Figure 3:
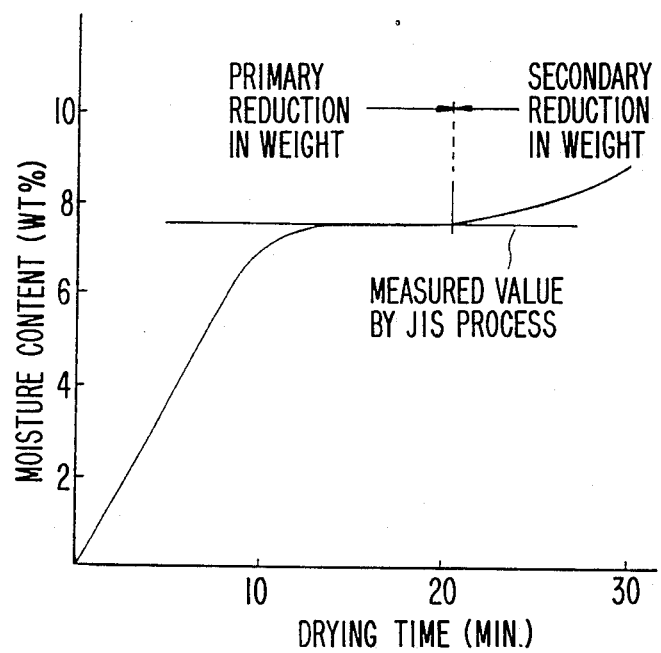
FIG. 3 is a diagram showing one example of a relationship between drying time and the results of measuring the moisture content in coal according to the illustrated embodiment.

One example of the results of measurement is shown in FIG. 3. As indicated in FIG. 3, simultaneously with the commencement of the measurement, a primary reduction in the weight of the sample begins. After about 15 minutes the sample attains a constant reduced weight. Then, after a while the sample undergoes a secondary reduction in weight. The reduction in weight before the constant reduced weight is attained is caused by an evaporation of moisture, and a moisture content value obtained at this time point was well consistent with the value obtained through the JIS process. It is to be noted that the secondary reduction in weight is caused by the decomposition of the coal, but it can be easily discriminated from the reduction in weight caused by drying.

In practice, at the time point when the primary reduction in weight of the sample has terminated and the weight of the sample has become constant, irradiation of microwaves, circulation of hot gases, the dehumidifying means and the turntable are stopped, the shutter is opened, and the sample is taken out. A series of these operations are automatically controlled by the sequence controller, a moisture content value is automatically calculated by the calculator on the basis of the weight of the sample and the reduced weight, and is digitally indicated by the digital indicator, and the moisture content value is transmitted as an electric signal to the boiler operating room. More specifically, in a conventional manner, the calculator 15 stores the initial weight of the sample as measured by weighing instrument 7 and converted to digital signals by A/D converter 14, checks whether the weight of the sample decreases by an amount less than a predetermined value during a predetermined time, stores the final weight of the sample as measured by weighing instrument 7, calculates the moisture content of the sample by performing the calculation: (initial wight-final weight)/initial weight, and issues signals representative of the results obtained from the above equation to the digital indicator 16 and display-recorder 17. The measuring time covering these processes is about 15 minutes, which can well satisfy the condition of 30 minutes or less which is necessary for achieving on-line analysis.

In this way, the moisture content measuring system according to the illustrated embodiment of the present invention is capable of measuring moisture content quickly and with a high degree of precision without being adversely influenced by the decomposition of coal.

As described in detail above, if the measure of employing microwaves and a hot wind in combination according to the present invention is practiced, it is possible to measure, for instance, the total moisture content of coal with precision equivalent to that in the JIS process. And moreover, in 15-20 minutes, the moisture content of coal can be analyzed on an on-line basis by automating a series of operations from the sampling of coal being conveyed to the measurement of a moisture content. And thus, a moisture content value changing moment to moment can be transmitted to a boiler operating room or the like. Accordingly, a very delicate operation control such as the regulation of a coal feed rate and a coal mixing proportion or the like can be greatly improved as compared to the prior art.

While a principle of the present invention has been described above in connection to one preferred embodiment of the invention, it is a matter of course that many apparently widely different embodiments of the present invention can be made without departing from the spirit of the present invention.

What is claimed is:

1. A moisture content measuring system for measuring the moisture content of a sample, said system comprising:
   a sample container for holding a sample;
   a weighing instrument, having a rotatable turntable adapted to support said sample container, for issuing analogue signals indicative of the weight of a sample held in said sample container while supported on said turntable;
   an A/D converter operatively connected to said weighing instrument for receiving the analogue signals issued thereby and converting the same to corresponding digital signals;
   a calculator operatively connected to said A/D converter for receiving the digital signals, for calculating the moisture content of the sample on the basis of the digital signals, and for issuing signals representative of the calculation;
   an indicator operatively connected to said calculator for receiving the signals issued by said calculator and for indicating results of moisture detection obtained by the signals so received;
   heating means including a hot gas generator for generating hot gas and for heating the sample by forcing the hot gas past the sample resulting in moisture evaporating from the heated sample into such hot gas; and
   dehumidifying means for removing moisture evaporated from the heated sample.

2. A moisture content measuring system as claimed in claim 1, wherein said dehumidifying means includes a heat exchanging device for cooling hot gas with which the sample has been heated by said hot gas generator.

3. A moisture content measuring system as claimed in claim 2, wherein said heat exchanging device includes a first heat exchanger for precooling hot gas with which the sample has been heated by said hot gas generator, and a second heat exchanger for cooling the hot gas pre-cooled by said first heat exchanger.

4. A moisture measuring system as claimed in claim 1, wherein said heating means further includes a magnetron for generating microwaves to heat the sample at a low temperature.

5. A moisture content measuring system as claimed in claim 4, wherein said hot gas generator includes a radiant heater and a fan for circulating gas past said radiant heater and said turntable.

6. A moisture content measuring system as claimed in claim 4, wherein said hot gas generator further includes a second radiant heater and a second fan for circulating gas past said radiant heater, said turntable and said dehumidifying means.

* * * * *